(12) United States Patent
Park et al.

(10) Patent No.: US 7,794,964 B2
(45) Date of Patent: Sep. 14, 2010

(54) BIOCHIP FOR THE DETECTION OF PHOSPHORYLATION AND THE DETECTION METHOD USING THE SAME

(75) Inventors: Sang-Hyun Park, Jeongeup-si (KR); Kyong Cheol Ko, Jeongeup-si (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 12/333,383

(22) Filed: Dec. 12, 2008

(65) Prior Publication Data
US 2009/0317849 A1 Dec. 24, 2009

(30) Foreign Application Priority Data
Jun. 24, 2008 (KR) .................... 10-2008-0059603

(51) Int. Cl.
*C12Q 1/48* (2006.01)
*C07K 14/00* (2006.01)

(52) U.S. Cl. .................... 435/15; 530/300; 530/350

(58) Field of Classification Search .................... None
See application file for complete search history.

(56) References Cited

OTHER PUBLICATIONS

Bulyk, M.L. et al, Quantifying DNA-protein interactions by double-stranded DNA arrays, Nature Biotechnology,1999, pp. 573-577, vol. 17.
Braunwalder, A. et al., A Solid-Phase assay for the Determination of Tyrosine Kinase Activity of c-src Using Scintillating Microtirtration, Analytical Biochemistry, 1996, pp. 23-26. vol. 234.
Houseman, B. et al., Peptide Chips for the Quantitative Evaluation of Protein Kinase Activity, Nature Biotechnology, 2002, pp. 270-274, vol. 20.
De Wildt, R. et al., Antibody Arrays for high-throughput screening of antibody-antigen interactions, Nature Biotechnology, 2000, pp. 989-994, vol. 18.
MacBeath, G. et al., Printing Proteins as Microarrays for High-throughput Function Determination, Science, 2000, pp. 1760-1763, vol. 289.
Haab, et al., Protein microarrays for highly parallel detection and quantitation of specific proteins and antibodies in complex situations, Genome Biology, 2001,pp. 1-13, vol. 2.
Zhu, H. et al., Analysis of yeast protein kinases using protein chips, Nature genetics, 2000, pp. 283-289, vol. 26.
Herengrother, P. et al., Small-Molecule Microarrays: Covalent Attachment and Screeing of Alcohol-Containing Small Molecules on Glass Slides, JACS, 2000, pp. 7849-7850, vol. 122.
Vijayendran, R. et al., A Quantitative Assessment of Heterogeneity for Surface-Immobilized Proteins, Analytical Chemistry, 2001, pp. 471-480, vol. 73.
Zhu, H. et al., Global Analysis of Protein Activities Using Proteome Chips, Science, 2001, pp. 2101-2105 , vol. 293.
Lesaicherre M. et al., Intein-Mediated Biotinylation of Proteins and Its Application in a Protein Microarray, JACS, 2002, pp. 8768-8769, vol. 124.
Hentz, N. et al., Bifunctional Fusion Proteins of Calmodulin and Protein A as Affinity Ligands in Protein Purification and in the Study of Proetin-Protein Interactions, Analytical Chemistry, 1996, pp. 3939-3944, vol. 68.
Hodneland, C. et al., Selective immobilization of proteins to self-assembled monolayers presenting active site-directed capture ligands, PNAS, 2002, pp. 5048-5052, vol. 99.
Kukar, T. et al., Protein Microarrays to Detect Protein-Protein Interations Using Red and Green Fluorescent Proteins, Analytical Biochemistry, 2002, pp. 50-54, vol. 306.
Hunter, T., Signaling—2000 and Beyond, Cell, 2000, pp. 113-127, vol. 100.
Zhang, Z.Y., Protein tyrosine phosphatases: prospects for therapeutics, Current Opinion in Chemical Biology, 2001, pp. 416-423, vol. 5.

*Primary Examiner*—Nashaat T Nashed
(74) *Attorney, Agent, or Firm*—Lucas & Mercanti, LLP

(57) ABSTRACT

The present invention relates to a biochip for detecting phosphorylation and a method for detecting phosphorylation using the same, more precisely a biochip prepared by integrating a protein produced from the recombination of a substrate of kinase selected from the group consisting of PKC (Protein Kinase C), cdc2-PK (cdc2 Protein Kinase) and DNA-PK (DNA-dependent Protein Kinase) and the elevated protein such as *Selenomonas ruminantium* membrane protein on a matrix surface coated with an active group, a kit for detecting phosphorylation composed of the said biochip and a cofactor labeled with a radio-isotope and a method for detecting phosphorylation using the same. The biochip for detecting phosphorylation of the present invention using a radio-isotope facilitates the detection of phosphorylation with a minimum amount of a sample by simple processes, compared with the conventional method using an antibody. Since this method can analyze a large amount of samples in a shorter period of time, it can be effectively used for the analysis of kinase activity.

12 Claims, 5 Drawing Sheets

FIGURE 1

```
AGAGCCTATGAGCCCTATGAGGTCCTGATGGATATCAGCCGCAAGCTCACGGATGTGGGGGTGTTGTACGGCGATTTCCT
CAATGTGCGCTATACCGGCGTATTGGAGGCGTTGCAAAACGGGGAATTTCCTGTGCGGGAAAAACATCTTTATGCCAAGA
GCGAAATGGTGCGGCTGCTGGATGATACCCTGTTTAAGGAAATCGATTTTGTGCCCGGCGCCCTGGACGATGATGAACAA
ATTGCCCGCAGCTGGGAAGAGCAGGGGTATGTGAATATCCAGCATGAAGTGGCTGTCAGCCCATATCTGTTCCGGGCTGC
TGTCAGCACTGCCAGCGTTGCTAATCTCAAGAGCCTATACACTCCGGAAGTACGTAAGGAACTGGCGCGGATTCTCCATC
GGATCGAGTATGACGTGCAGCGGGCGGATAATATAATGCGGCTGCAACAACTGTGCAAACAGGAAGGCATTTTCTCAGAG
TATTTGCAGGATTTTATAGAAGAAACATGTTATCATGCAAATGAAGTAAAACATTTGTTGCCAGATGAACAATGAGACTC
AAAGTCAAATAAAAGTTGTCAGACAC TTGCAA ATTGCTATTATCTATGA TAAAAT TAGCGTTGTCTTGGAAATGGATTAG
GATTTGCTGAGGAAACATGGACACTCATGGAAAGAATAATCCGCCTTCAAGACGAGTACTAACACTATTTATTGAAGGAG
GAGTTTCTT ATGAAGAAGACTCTCGTATCCGCTCTGACGACCGCTCTGGTTGTTGGTGCAGCTAGCACGACGTTTGCT GC
          M  K  K  T  L  V  S  A  L  T  T  A  L  V  V  G  A  A  S  T  T  F  A   A
TAGCAAC CGTTCTCCGATGTTCCTGCTGATCATTGGGCTTATGACGCTGTAGCTCAGCTGGCTGCTGACGGCGTTGTTG
  S  N  P  F  S  D  V  P  A  D  H  W  A  Y  D  A  V  A  Q  L  A  A  D  G  V  V  E
AAGGTTATGGCGACAGCACCTTCAAGGGCAACCGTAACATCACTCGTTACGAAATGGCT CAGATGGTTGCTAAAGCTATG
  G  Y  G  D  S  T  F  K  G  N  R  N  I  T  R  Y  E  M  A  D  M  V  A  K  A  M
GCTAAGAACACTTCCGGCACGGACAAGGCTCTGGTTGACAAACTGGCTGCTGAATTCGCAGAAGAACTCAACAACCTCG
  E  A  K  N  T  S  G  T  D  K  A  L  V  D  K  L  A  A  E  F  A  E  L  N  N  L  G
GTGTTCGCGTAAGCAACCTCGAACGCAATGCTGACATGGTTAAA TGGAATGGCGTTGCTGAGTACACCTTCACGCGTCAG
  V  R  V  S  N  L  E  R  N  A  D  M  V  K  W  N  G  V  A  E  Y  T  F  T  R  Q
CGTCATGAAAAAAATGGCAAAAAGACGACGAATCATGGCGACGACAATGTACTGTTCCGTCTCGAGCCCTCCGCTGAAGT
  R  H  E  K  N  G  K  K  T  T  N  H  G  D  D  N  V  L  F  R  L  E  P  S  A  E  V
TAACAGCCATTGGCATGTAAAGGCTCGTCTCGATGCTAACTCCAACCTGAAATCTGACCAGGGTGAAGATAGCAGCAGCG
  N  S  H  W  H  V  K  A  R  L  D  A  N  S  N  L  K  S  D  Q  G  E  D  S  S  S  V
TTAAGCTGAAACGTGTATGGGCTCAGGGTGAATATGGCAAACTGACGGTTAAACTCGGTAAGTTTGCTTGCCTGAACGAC
  K  L  K  R  V  W  A  Q  G  E  Y  G  K  L  T  V  K  L  G  K  F  A  S  L  N  D
GATACCTTTGCTGATACGCCGTTCTCCGGTGCTGAAGTTTCCTACGGCAAGGATGTTAAAGTCATTGCTGCTGCTGGTCG
  D  T  F  A  D  T  P  F  S  G  A  E  V  S  Y  G  K  D  V  K  V  I  A  A  A  G  R
TCTGAACCTTTGGGATGCTAGTGCATTTAAGAAGAATGTAGACATCCAGAATGTTCGTAATTGGATGGTTGCTGGTCGTC
  L  N  L  W  D  A  S  A  F  K  K  N  V  D  I  Q  N  V  R  N  W  M  V  A  G  R  H
ACGATGATAGAACTGCAAACTATCAGTATGCTGGTCTCGAACTCAACAAGAGCAAGCTGAGCGGTGGCCTGTACTGGCAT
  D  D  R  T  A  N  Y  Q  Y  A  G  L  E  L  N  K  S  K  L  S  G  G  L  Y  W  H
CACCTGAACGCAGCAGGTTTCGATTATAAGAAAGGTACGACGGATGAAGCTAATATCGGTGCAGTAAAAGGCAGCTACAC
  H  L  N  A  A  G  F  D  Y  K  K  G  T  T  D  E  A  N  I  G  A  V  K  G  S  Y  T
CTTTAGCAAGAATGTCAGCGTAAATGGTTTCTATACTCAGAACTTTGATGTTGATACCAAGAATTATCAGGATAAGTCCG
  F  S  K  N  V  S  V  N  G  F  Y  T  Q  N  F  D  V  D  T  K  N  Y  Q  D  K  S  A
CTAGCCTCGAAGTAGACTATAAGGGCGCTCAGCAGGAAAACAAGGGTACTTGGGGTGCTTGGGTTGCATACCGTCGCCTT
  S  L  E  V  D  Y  K  G  A  Q  Q  E  N  K  G  T  W  G  A  W  V  A  Y  R  R  L
GGTAACGCCGCAATCATCAACAACACGTACGATGTTATCAATACGGGCTACAAAGGTTGGGAAGTTGGCGGTAACTACAC
  G  N  A  A  I  I  N  N  T  Y  D  V  I  N  T  G  Y  K  G  W  E  V  G  G  N  Y  T
GCTCTTCAAGAACGTTGTAACGACTCTCCGTTATGGCAACCAGAAGGATATCAGCAACTCCAACGTTAAGGACCAGAATT
  L  F  K  N  V  V  T  T  L  R  Y  G  N  Q  K  D  I  S  N  S  N  V  K  D  Q  N  F
TCTTCGGTCGCGTTCAGTTCTTCTTC TAATCCTGAGATTAGCAGATTATACGCAAATAACAAAGACCTCCGTTGTGGCGG
  F  G  R  V  Q  F  F  F  *
AGGTCTTTTCTTGCAATAAGCAGGGATTTGTAGTAGAATGAACATAGATAAAAAAAAGACCACCGATAGACGGCTAGTTTC
CACGCTCGATGGTTAATAGCTTAATAAGAAACAGAAATAACCGTCAAGCTTGGACCCTTGGGCGGTTATTTTTGTTTCAG
GACAATGATGATAAGCAACAGCATCAAAAGCTGGAAAGACA
```

Detection using phosphorylation by [γ −32P]ATP

FIGURE 4
(A)           (B)
a    b      a    b
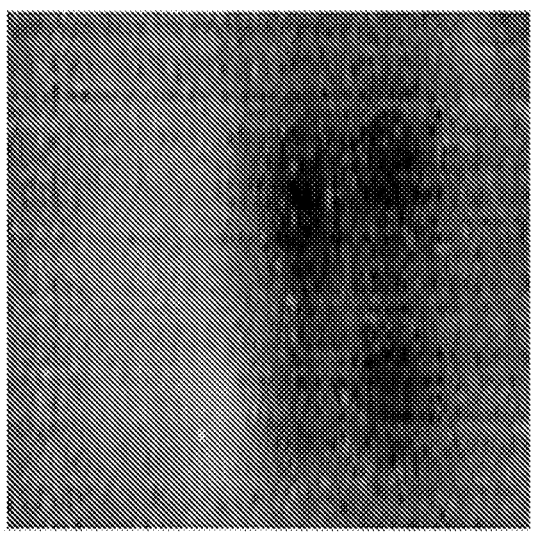

US 7,794,964 B2

BIOCHIP FOR THE DETECTION OF PHOSPHORYLATION AND THE DETECTION METHOD USING THE SAME

CROSS-REFERENCES TO RELATED APPLICATION

This patent application claims the benefit of priority under 35 U.S.C §119 of Korean Patent Application No. 10-2008-0059603 filed on Jun. 24, 2008, the contents of which are incorporated herein by reference.

BACKGROUND OF THE INVENTION

1. Field of the Invention

The present invention relates to a biochip for detecting phosphorylation and a method for detecting phosphorylation using the same, more precisely a biochip prepared by integrating a fusion protein produced from the recombination of a substrate of a kinase selected from the group consisting of PKC (Protein Kinase C), cdc2-PK (cdc2 Protein Kinase) and DNA-PK (DNA-dependent Protein Kinase), and the elevated protein such as *Selenomonas ruminantium* membrane protein on a matrix surface coated with an active group, a kit for detecting phosphorylation composed of the said biochip and a cofactor labeled with a radio-isotope and a method for detecting phosphorylation using the same.

2. Description of the Related Art

Recent biotechnology industry is characterized by the fusion of biology with related technologies in the fields of electronics, computer science and mechanical engineering. Biological studies require a new system to approach an individual biological subject as a whole and also require a novel approaching method performing experiments in a large scale with a small amount of samples. Accordingly, a biochip is expected to play a crucial role in the field of bioinformation analysis using genes, proteins and cells and in use of the bioinformation.

According to the completion of human genome project, studies on micro-analysis system such as DNA chip or protein chip for the analysis of genes or proteins are actively undergoing in the overall biological industry. Biochip market is expected to be growing greatly and has been a major target of development in bio-industry in Korea.

Protein chip or peptide chip is a kind of automatic analysis device for simultaneous analysis of tens or thousands of proteins or peptides fixed on a small matrix, which is the next generation biosensor different from DNA chip in analysis mechanism and applying field. Protein chip is a key technique to disclose functions of biomolecules interacting specifically to specific proteins and to develop a novel method for preventing and treating disease, particularly those diseases untreatable so far by the conventional arts, based on functional analysis and network analysis of protein.

Protein chip techniques are largely divided into three categories; protein microarray techniques related to chip production, analysis techniques for quantitatively measuring and comparing interactions between proteins by observing proteins fixed on array and application techniques of protein chip. The first core technique, protein microarray chip is prepared by different methods according to techniques to analyze protein chip. For example, in the case of using SPR (Surface Plasmon Resonance), proteins have to be fixed on a thin metal film such as a thin gold film. Therefore, a thin gold film construction method and a protein fixation technique have to be developed together. In the case of using a fluorescent material, proteins are fixed directly on a slide glass for analysis. So, the proteins have to be labeled with fluorescent materials.

The second core technique, the analysis technique of protein chip includes SPR, mass spectrometry, fluorometry, electrochemical analysis method and nano-imaging technique such as Ellipsometry, which has been developed very competitively so far. Fluorometry based on DNA chip analysis has been most widely used so far, but each method has been recognized to have merits and demerits, and which protein chip analysis method is most appropriate for disease is still undecided.

The last core technique, the application technique of protein chip has the biggest potential for the development and still leaves a lot to discover.

The newly developed techniques related to protein chip are classified into four categories as follows.

(1) A technique to analyze interaction between DNA and protein on the chip by using DNA microarray. On the chip, single-stranded oligonucleotide is converted into double-stranded oligonucleotide, to which specific DNA sequence restriction enzyme is reacted. Then, DNA-protein interaction was examined by measuring digestion. So, this technique is effective in identifying a novel DNA binding protein and in disclosing the characteristics thereof (Bulyk, M. L. et al., *Nature. Biotechnol.*, 17:573-577, 1999).

(2) A technique to analyze diverse enzymes including restriction enzyme, peroxidase, phosphatase and protein kinase, and antigen-antibody reaction on the chip (US Patent Publication No. 2002/0055186A1; WO 01/83827A1; Braunwalder A. et al., *Anal. Biochem.*, 234:23-26, 1996; Houseman B. et al., *Nature Biotechnol.*, 20:270-274, 2002; Ruud M. et al., *Nature Biotechnol.*, 18:989-994, 2000). In particular, this technique can be applied in mass-analysis, biochemical analysis, new drug candidate analysis and disease diagnosis by examining protein-protein interaction, kinase-peptide substrate reaction and protein-ligand binding reaction. However, when a kinase specific substrate peptide or a low-molecular weight protein is fixed, bovine serum albumin (BSA) is necessarily added in order to prevent non-specific fixation, which buries the protein fixed thereon. Besides, when different antibodies are fixed on the chip to be reacted with fluorescein labeled antigen mixture, only 60% of the antibodies were quantified and only 23% of the antibodies were qualified (MacBeath G. et al., *Science*, 289:1760-1763, 2000; Haab B. et al., *Genome Biol.* 2: research 0004, 2001).

(3) A technique to analyze massive proteins expressed on the chip from cDNA library (WO 01/83827, WO 02/50260). This technique is effective in large scale measurement of biochemical activity of a protein (Heng Zhu, et al., *Nature genetics*, 26:283-289, 2000).

(4) A method to analyze a sample by using the technique of regulating orientation of biomolecules at molecular level using affinity tag and forming a stable and single layer of biomolecules on the surface of the chip (US Patent Publication No. 2002/0055125A1; U.S. Pat. No. 6,406,921; Paul J. et al., *JACS*, 122:7849-7850, 2000; RaVi A. et al., *Anal. Chem.*, 73:471-480, 2001; Benjamin T. et al., *Tibtech.*, 20:279-281, 2002). For example, a protein is expressed as a His-tag fusion protein, which is reacted to a chip fixed with Ni-NTA functional group, leading to fixation. The protein is then expressed as an intein fused protein or retains the activity, which not only makes the purification easy but also makes the protein on the chip more stable and active by fixing in a regular direction on the avidin treated chip (Zhu et al., *Science*, 293:2101-2105, 2001; Marie-Laure L. et al., *JACS* 124:8768-8769, 2002). And, the protein is expressed on the chip as a fusion protein using a supporter specific protein (calmodulin, etc) and tag (poly cysteine, lysine, histidine, etc) and fixed. The protein is purified by using protein-protein interaction and further used for SPR (surface plasmon resonance) and FACS (fluorescence activated cell sorter) (Hentz et al., *Anal. Chem.*, 68:3939-3944, 1996; Hodneland et al., *PNAS*, 99:5048-5052, 2002; Kukar et al., *Anal. Biochem.*, 306:50-54, 2002; U.S. Pat. No. 6,117,976).

Kinase is a protein enzyme involved in signal transduction pathways to induce a series of reactions in vivo and hence it is considered to be an effective target for a drug. Kinase provides γ-phosphorylated group to serine, threonine and tyrosine residues of the specific sequence of a target protein from ATP provided in cells, by which it is involved in signal transduction pathway in eukaryotic cells and various diseases (Hunter, T., *Cell* 100:113-127, 2000; Zhang, Z. Y., *Curr. Opin. Chem. Biol.* 5:416-423, 2001). The conventional method to study the activity of kinase is to examine cell membrane using a radio-isotope, but this method is very slow-going and requires a great labor. Another conventional method to measure kinase and its receptor in a large scale is ELISA (enzyme-linked immunosorbent assay) or a method using antibody. ELISA is a comparatively accurate method but takes a lot of time and requires a huge amount of samples. The method using an antibody facilitates mass-analysis but requires high costs and the processes are very complicated.

Promega Co., USA provides a phosphorylation assay kit using a membrane having high absorptiveness to ATP labeled with a radio-isotope and biotinated kinase substrate. However, this kit is limited in mass-analysis. This company also provides an analysis method without using a radio-isotope but using moving difference on electrophoresis caused by changes of net charge of the substrate after phosphorylation of kinase. But, this method requires high costs for mass-analysis. Except for the said four protein chip related techniques, there is no method available for screening the activity of protein kinase in a large scale by using protein chip or peptide chip. Therefore, it is urgently required to develop a new system facilitating accurate and fast analysis with low costs.

The present inventors constructed a biochip for the detection of phosphorylation in Korean Patent Application No. 2007-0070049, in which kinase substrate is integrated on the surface of a matrix directly or as a fusion protein fused to *E. coli* malic enzyme, but further studies on the biochip using PKC (Protein Kinase C), cdc2-PK (cdc2 Protein Kinase) or DNA-PK (DNA-dependent Protein Kinase) substrate are required.

Thus, the present inventors further studied and constructed a recombinant fusion protein from the fusion of PKC, cdc2-PK or DNA PK substrate with *Selenomonas ruminantium* membrane protein and then completed this invention by constructing a protein chip on which the recombinant fusion protein is integrated on a matrix surface coated with an active group and measuring phosphorylation by the kinase.

SUMMARY OF THE INVENTION

It is an object of the present invention to provide a biochip constructed by integrating a fusion protein prepared by the recombination of a kinase substrate selected from the group consisting of PKC (Protein Kinase C), cdc2-PK (cdc2 Protein Kinase) and DNA-PK (DNA-dependent Protein Kinase) with the elevated protein, *Selenomonas ruminantium* membrane protein on a matrix surface coated with an active group, and a kit for detecting phosphorylation composed of the said biochip and a cofactor labeled with a radio-isotope, and a method for detecting phosphorylation using the same.

The biochip for detecting phosphorylation and the method for detecting phosphorylation using the same of the present invention increase sensitivity by using a radio-isotope, by which a smaller amount of a sample can be used by simpler processes, compared with the conventional method. In addition, the method of the present invention produces a very clear result owing to a simplified procedure excluding blocking process for preventing non-specific fixation on the chip. So, using the biochip of the present invention has advantages of saving time and having economical efficiency. According to the present invention, only a small amount of a sample is required, suggesting that the size of a spot is very small, indicating the number of samples that can be integrated on the surface can be increased, which enables fast analysis of a large amount of samples within a short period. Therefore, the method of the present invention can be effectively used for the analysis of kinase activity.

BRIEF DESCRIPTION OF THE DRAWINGS

The application of the preferred embodiments of the present invention is best understood with reference to the accompanying drawings, wherein:

FIG. 1 is a diagram showing the nucleotide sequence (SEQ ID NO: 17) of Mep45 derived from *Selenomonas ruminantium* and the amino acid sequence (SEQ ID NO: 10), the digestion site by the treatment of proteinase K, derived therefrom:

Box: promoter, SLH domain, porin homology region; and

Arrow: digestion site by the treatment of proteinase K in the whole cell.

Figure 2:
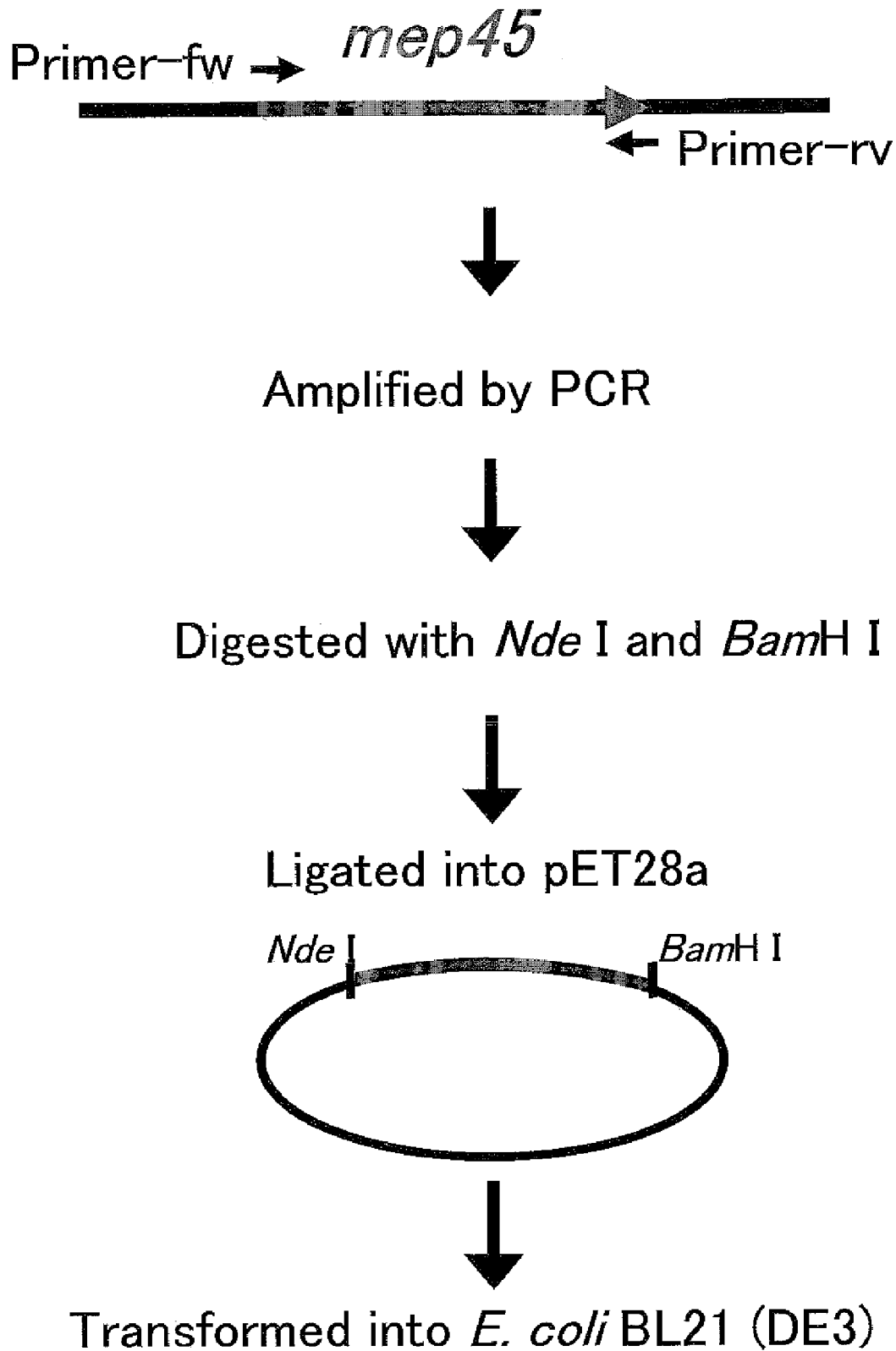

FIG. 2 is a diagram illustrating the cloning process of the recombinant Mep45-kinase substrate fusion protein.

Figure 3:
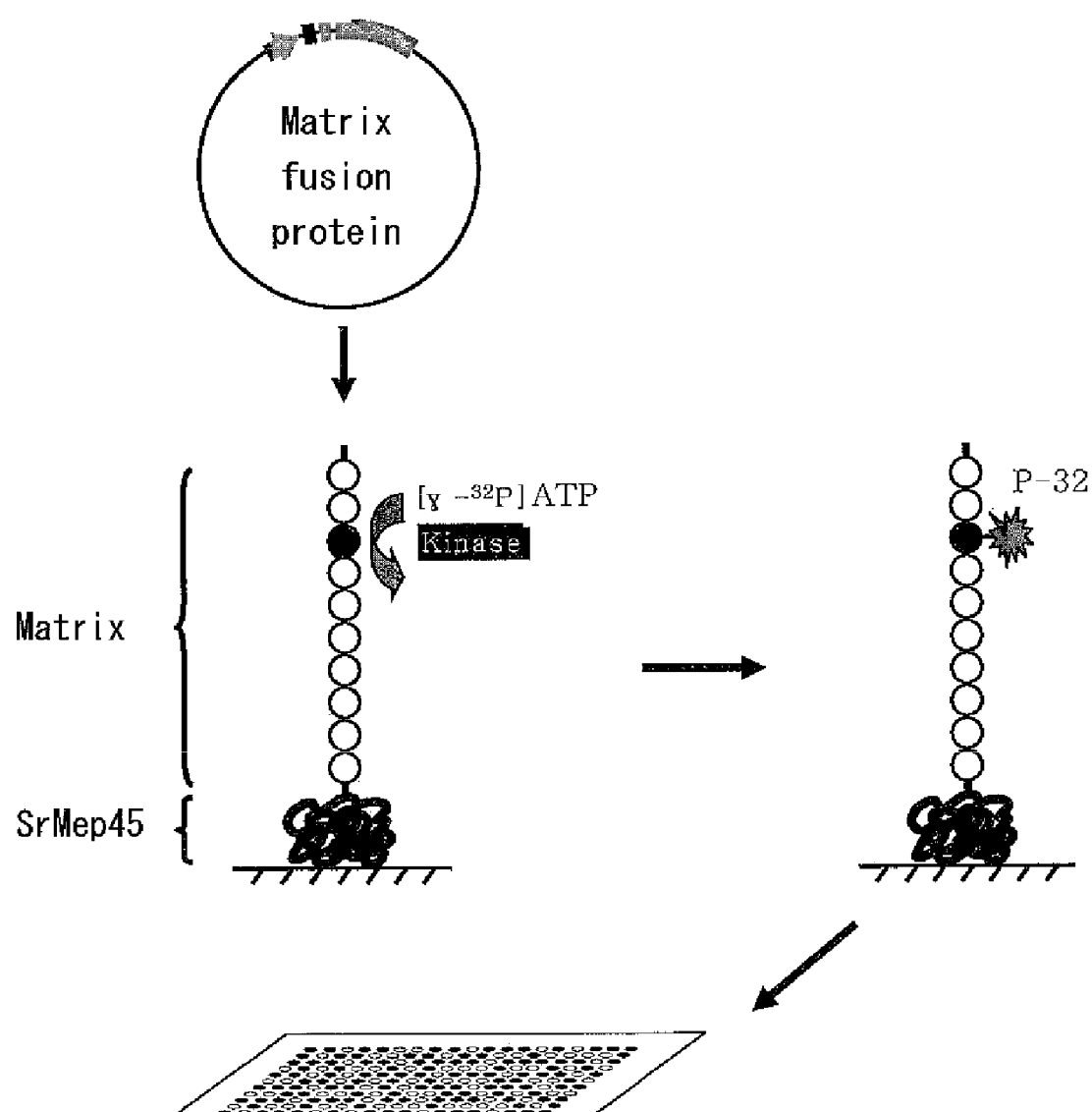

FIG. 3 is a diagram illustrating the phosphorylation of kinase-substrate using [γ-$^{32}$P]ATP.

FIG. 4 is a diagram illustrating the phosphorylation of cdc2 protein kinase and peptide substrate using [γ-$^{32}$P]ATP:

(A) a: negative control (BSA), b: cdc2 protein kinase (peptide); and (B) a: negative control (BSA), b: cdc2 protein kinase substrate (Mep45 fusion substrate).

Figure 5:
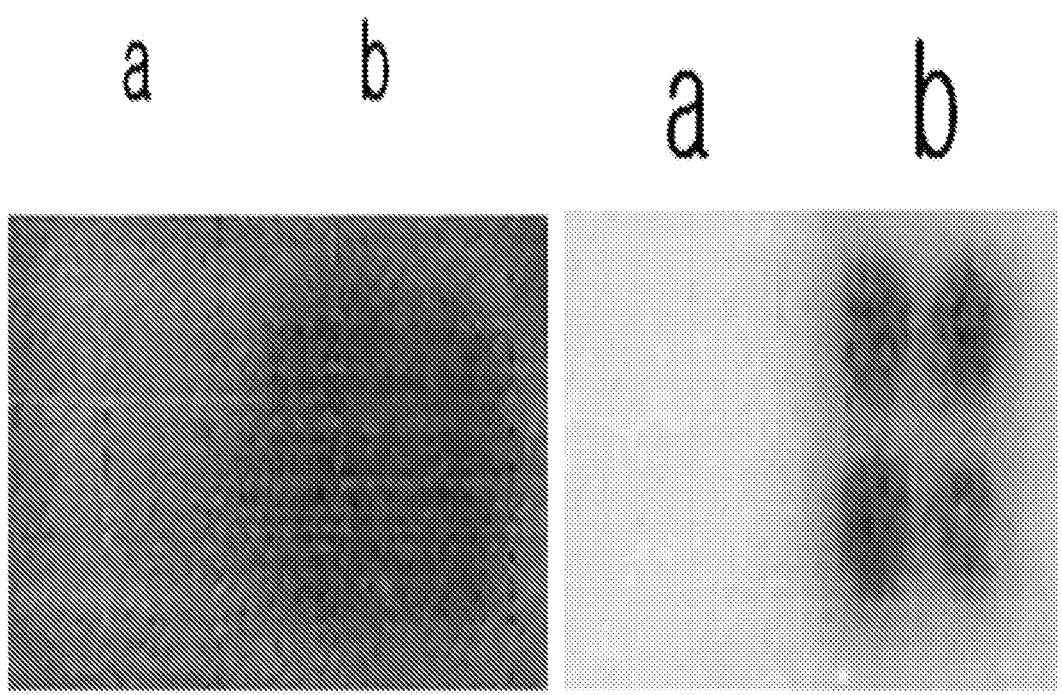

FIG. 5 is a diagram illustrating the phosphorylation of PKC (protein kinase C) and peptide substrate using [γ-$^{32}$P]ATP:

(A) a: negative control (BSA), b: PKC (peptide); and (B) a: negative control (BSA), b: PKC substrate (Mep45 fusion substrate).

DESCRIPTION OF THE PREFERRED EMBODIMENTS

To achieve the above object, the present invention provides a biochip comprising a fusion protein integrated on a matrix surface coated with an active group, wherein, the fusion protein is prepared by the fusion of a substrate of a kinase having one of amino acid sequences represented by SEQ. ID. NO: 1-NO: 3 with an elevated protein, wherein the elevated protein is *Selenomonas ruminantium* membrane protein.

The present invention also provides a kit for the detection of phosphorylation containing the biochip of claim 1 and [γ-$^{32}$P]ATP.

The present invention further provides a detection method of phosphorylation comprising the following steps:

1) mixing a sample with [γ-$^{32}$P]ATP;
2) inducing phosphorylation by treating the biochip of claim 1 with the mixed sample of step 1);
3) washing the biochip of step 2); and
4) measuring phosphorylation by observing signals from the biochip of step 3) using X-ray film and phosphorimager.

Hereinafter, the present invention is described in detail.

The present invention provides a biochip comprising a fusion protein integrated on a matrix surface coated with an active group,
wherein, the fusion protein is prepared by the fusion of a substrate of a kinase having one of amino acid sequences represented by SEQ. ID. NO: 1-NO: 3 with an elevated protein.

The material of the matrix of the biochip of the present invention is preferably selected from the group consisting of glass, plastic, metal and silicon, and glass is more preferred, but not always limited thereto.

The active group coated on the matrix of the biochip of the present invention plays a role in fixing a peptide and is preferably selected from the group consisting of amine group, aldehyde group, carboxyl group and thiol group, and aldehyde group is more preferred, but not always limited thereto. In fact, almost every active group known to those in the art as an active group capable of fixing a protein molecule on a matrix can be used.

The kinase substrate of the biochip of the present invention is preferably the substrate (AAKIQASFRGHMARKK; SEQ. ID. NO: 1, PKTPKKAKKL; SEQ. ID. NO: 2, or EPPLSQQAFADLWKK; SEQ. ID. NO: 3) for PKC (Protein Kinase C), cdc2-PK (cdc2 Protein Kinase) or DNA-PK (DNA-dependent Protein Kinase), but not always limited thereto.

The elevated protein of the biochip herein is preferably *Selenomonas ruminantium* membrane protein (SrMep45, SEQ. ID. NO: 10), but not always limited thereto.

The kinase substrate herein is fixed on the biochip of the present invention as the elevated protein-substrate fusion protein, but not always limited thereto.

On the biochip of the present invention, the diameter of the integrated spot is preferably 100~300 μm and the distance between the spots is preferably 300~500 μm, but not always limited thereto.

The present inventors prepared a recombinant fusion protein using substrates of PKC (Protein Kinase C), cdc2-PK (cdc2 Protein Kinase) or DNA-PK (DNA-dependent Protein Kinase) and *Selenomonas ruminantium* membrane protein. Then a biochip was constructed by fixing the recombinant fusion protein on the surface of a slide glass treated with aldehyde group, the functional group fixable protein only, by spotting method (see FIG. 2).

The biochip of the present invention does not need blocking process which is necessary for the conventional methods. The blocker such as BSA (Bovine Serum Albumin) causes the burial of proteins fixed on a matrix surface. BSA is used for the prevention of non-specific fixation observed during the fixation of a kinase specific peptide or a low molecular protein. So, using the biochip of the present invention makes the process simple and has advantages of saving time and having economical efficiency.

To confirm the phosphorylating conditions of kinase-substrate using [γ-$^{32}$P]ATP, the biochip prepared above was treated with kinase buffer containing [γ-P]ATP and phosphorylation between Mep45-kinase substrate fusion protein and kinases was induced. Then, the phosphorylation was measured by using X-ray film and phosphorimager (see FIG. 3).

As a result, there was no signal observed on the spot of BSA, the negative control, while signals were observed on both the spots of substrates of PKC (Protein Kinase C), cdc2-PK (cdc2 Protein Kinase) or DNA-PK (DNA-dependent Protein Kinase) and the spots of substrate-SrMep45 fusion protein. The results indicate that substrates of PKC (Protein Kinase C), cdc2-PK (cdc2 Protein Kinase) or DNA-PK (DNA-dependent Protein Kinase) and the radio-isotope [γ-$^{32}$P]ATP of the present invention can be used for the measurement of phosphorylation (see FIGS. 4 and 5).

The present invention also provides a kit for the detection of phosphorylation containing the said biochip and [γ-$^{32}$P]ATP.

The kit herein can measure phosphorylation of a kinase selected from the group consisting of PKC (Protein Kinase C), cdc2-PK (cdc2 Protein Kinase) and DNA-PK (DNA-dependent Protein Kinase), but not always limited thereto.

Preferably, the kit additionally contains protein kinase as a positive control.

The present invention further provides a detection method of phosphorylation comprising the following steps:
1) mixing a sample with [γ-$^{32}$P]ATP;
2) inducing phosphorylation by treating the biochip of claim 1 with the mixed sample of step 1);
3) washing the biochip of step 2); and
4) measuring phosphorylation by observing signals from the biochip of step 3.

In the above method, the sample of step 1) can be selected from the group consisting of extracts of cells and tissues, fractions or cell culture solutions, cell lysates, crude extracts of cells or tissues, exudates such as urine, sweat, saliva and tear, and body fluids such as blood, plasma, lymph and serum, but not limited thereto and any biological sample known to those in the art can be used.

In this method, the sample and the biochip of step 2) are preferably reacted in a 30° C. or 37° C. humid chamber for 30 minutes-1 hour, and one hour reaction is more preferred, but not always limited thereto, and the reaction time can be varied according to the specificity between substrates and kinases in the sample.

In this method, the measurement of phosphorylation in step 4) is performed by using X-ray film or phosphorimager, but not always limited thereto. Sensitization time for the measurement is 12-24 hours, but not always limited thereto, and can be varied according to the specificity between substrates and kinases in the sample.

The method for detecting phosphorylation of the present invention has advantages of a simple process of chip surface treatment for substrate fixation and fast and easy measurement, compared with the conventional fluorescence ELISA, because the one-pot labeled radio-isotope can be detected as it is. According to the conventional fluorescence detection method, a specific amino acid of substrate has to be phosphorylated first, and then the phosphorylated amino acid region is reacted with a secondary antibody labeled with fluorescent materials, which is an indirect detection method that cannot provide precise quantification at a satisfactory level. However, the method for detecting phosphorylation of the present invention is characterized by direct labeling of a radio-isotope to the substrate, so that the method not only facilitates precise quantification of detection result but also facilitates detection with a minimum amount of samples with high sensitivity.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Elevated Protein-Substrate Fusion Protein

<1-1> Cloning of SrMep45-Substrate Fusion Protein

To prepare SrMep45 (Selenomonas ruminantium membrane protein)-substrate fusion protein, the PCR product obtained by PCR amplification with chromosome DNA of *Selenomonas ruminantium* subsp. *lactilytica*, ATCC 19205) (Kanegasaki, S., and Takahashi, H., *J. Bacteriol.* 93, 456-463, 1967) and plasmid were cloned (FIG. 1).

For the cloning of each substrate (AAKIQASFRGH-MARKK; SEQ. ID. NO: 1, PKTPKKAKKL; SEQ. ID. NO: 2, or EPPLSQQAFADLWKK; SEQ. ID. NO: 3) for PKC (Protein Kinase C), cdc2-PK (cdc2 Protein Kinase) and DNA-PK (DNA-dependent Protein Kinase), PCR was performed using pSrMep45 as a template with primers PKC-Fw-Nde (5'-CATCATATGGCTGCTAAAATTCAAGCT-TCTTTTCGTGGTCATATGGCTCGTAAAAAAGCTAGC-AACCCGTTCTCCGATG-3'; SEQ. ID. NO: 4), PKC-Rv-Bam (5'-GACGGATCCTTATTTTTTACGAGC-CATATGACCACGAAAAGAAGCT-TGAATTTTAGCAGCGAAGAAGAACTGAACGCGAC-CGAAG-3'; SEQ. ID. NO: 5), cdc2-MP-Fw-Nde (5'-CAT-CATATGCCTAAAACTC-CTAAAAAAGCTAAAAAACTTGCTAG-CAACCCGTTCTCCGATG-3'; SEQ. ID. NO: 6), cdc2-MP-Rv-Bam (5'-GACGGATCCTTAAAGTTTTTTAGCTTTTT-TAGGAGTTTTAGGGAAGAAGAACT-GAACGCGACCGAAG-3'; SEQ. ID. NO: 7), DNA-PK-MP-Fw-Nde (5'-CATCATATGGAACCTCCTCTTTCTCAA-CAAGCTTTTGCTGATCTTTGGAAAAAAGCTAGCAA-CCCGTTCTCCGATG-3'; SEQ. ID. NO: 8) and DNA-PK-MP-Rv-Bam (5'-GACGGATCCTTATTTTTTCCAAAGAT-CAGCAAAAGCTTGTTGAGAAAGAGGAG-GTTCGAAGAAGAACTGAACGCGACCGAAG-3'; SEQ. ID. NO: 9) (Table 1). The PCR was performed using 2.0 unit Taq DNA polymerase (50 mM KCl, 10 mM Tris-HCl, pH 9.0, 1.5 mM $MgCl_2$, 0.01% gelatin, 0.1% Triton X-100), 0.4 mM dNPT (deoxyribonucleotide triphosphate) and the reaction mixture containing the said primer set with Palm-cycler (Corbett Life Science, USA) as follows: at 94° C. for 5 minutes (1 cycle); and at 94° C. for 1 minute, at 55° C. for 1 minute, and at 72° C. for 1 minutes (30 cycles); and then at 72° C. for 5 minutes (1 cycle). The PCR product was electrophoresed on 0.8% agarose gel, followed by staining with SYBR Green I. The amplified right size DNA was purified by using Gel Extraction Spin Column (Bio-Rad Lab., USA). The amplified DNA was ligated to plasmid pGEM-T Easy vector, followed by sequencing. The subcloned sample was digested with NdeI and BamI, which was ligated to pET-28a predigested with the same enzymes. *E. coli* BL21 (DE3) was transformed with the vector. As a result, a new strain for the production of the recombinant Mep45-kinase substrate fusion protein was generated (FIG. 2).

TABLE 1

Target kinase matrix and primer for cloning thereof

| Matrix | Primer | Sequence | SEQ. ID. NO: |
|---|---|---|---|
| PKC (Protein Kinase C) matrix | PKC-Fw-Nde | 5'-CAT CAT ATG GCT GCT AAA ATT CAA GCT TCT TTT CGT GGT CAT ATG GCT CGT AAA AAA GCT AGC AAC CCG TTC TCC GAT G-3' | SEQ. ID. NO: 4 |
| | PKC-Rv-Bam | 5'-GAC GGA TCC TTA TTT TTT ACG AGC CAT ATG ACC ACG AAA AGA AGC TTG AAT TTT AGC AGC GAA GAA GAA CTG AAC GCG ACC GAA G-3' | SEQ. ID. NO: 5 |
| cdc2-PK (cdc2 Protein Kinase) matrix | cdc2-MP-Fw-Nde | 5'-CAT CAT ATG CCT AAA ACT CCT AAA AAA GCT AAA AAA CTT GCT AGC AAC CCG TTC TCC GAT G-3' | SEQ. ID. NO: 6 |
| | cdc2-MP-Rv-Bam | 5'-GAC GGA TCC TTA AAG TTT TTT AGC TTT TTT AGG AGT TTT AGG GAA GAA GAA CTG AAC GCG ACC GAA G-3' | SEQ. ID. NO: 7 |
| DNA-PK (DNA-dependent Protein Kinase) matrix | DNA-PK-MP-Fw-Nde | 5'-CAT CAT ATG GAA CCT CCT CTT TCT CAA CAA GCT TTT GCT GAT CTT TGG AAA AAA GCT AGC AAC CCG TTC TCC GAT G-3' | SEQ. ID. NO: 8 |
| | DNA-PK-MP-Rv-Bam | 5'-GAC GGA TCC TTA TTT TTT CCA AGG ATC AGC AAA AGC TTG TTG AGA AAG AGG AGG TTC GAA GAA GAA CTG AAC GCG ACC GAA G-3' | SEQ. ID. NO: 9 |

Vectors encoding the final Mep45-substrate fusion protein were pMep45PKC1, pMep45PKC2, pMep45cdc21, pMep45cdc22, pMep45DPK1 and pMep45DPK2, as shown in Table 2.

TABLE 2

Cloned vector for each Mep45-substrate fusion protein

| Matrix | Cloned vector | Structure |
|---|---|---|
| PKC substrate | pSrMep45PKC1 (SEQ ID NO: 11) | •-□ |
|  | pSrMep45PKC2 (SEQ ID NO: 12) | •-□-• |
| cdc2-PK substrate | pSrMep45cdc21 (SEQ ID NO: 13) | ♦-□ |
|  | pSrMep45cdc22 (SEQ ID NO: 14) | ♦-□-♦ |
| DNA-PK substrate | pSrMep45DPK1 (SEQ ID NO: 15) | ▲-□ |
|  | pSrMep45DPK2 (SEQ ID NO: 16) | ▲-□-▲ |

□: SrMep45;
•: PKC substrate;
♦: cdc2-PK substrate; and
▲: DNA-PK substrate.

<1-2> Production and Purification of Recombinant Mep45-Kinase Substrate Fusion Protein The strain prepared in Example <1-1> was cultured in 200 ml of LB medium (tryptone 10 g/L, yeast extract 5 g/L, NaCl 5 g/L) in a 500 ml Erlenmeyer flask at 30° C. with 200 rpm. The antibiotic kanamycin was added at the final concentration of 50 μg/ml. The cells were cultured until O.D.$_{660}$ reached 0.4. IPTG was added at the final concentration of 0.1 mM, followed by further culture at 30° C. with 200 rpm for 3 hours. Upon completion of the culture, the cells were collected (8,000 rpm, 10 minutes, 4° C.). The collected cells were suspended in PBS (200 mM NaCl, 3 mM KCl, 2 mM KH$_2$PO$_4$, 1 mM Na$_2$HPO$_4$, pH 7.5) and lysed using ultrasonicator. Cell debris was eliminated by centrifugation. The recombinant Mep45-kinase substrate fusion protein was purified by using Ni-chelating resin (GE Healthcare, Sweden) to 6-histidine tag. The purified protein was quantified according to Bradford method using BSA (bovine serum albumin) as a standard.

The mass of the SrMep45-substrate protein was approximately 45 kDa, which was bound to the aldehyde group on a surface of the slide to protect active site of the substrate being apt to be buried by BSA used in blocking stage.

Example 2

Construction of Biochip

To fix substrate on the aldehyde-treated slide glass (Nuricell Inc., Korea), 0.1 mg/ml of the Mep45-kinase substrate fusion protein or 1.25 μg/ml of peptide substrate (Promega, Madison, Wis.) was integrated. Particularly, the recombinant Mep45-kinase substrate fusion protein solution (10% glycerol, PBS, pH 7.5) was prepared at the concentration of 0.1 mg/ml, and this substrate solution was integrated on the aldehyde-treated slide glass at the spot intervals of 300 μm by using microarray device (Genetix Ltd, UK). The size of the spot was regulated to be 300 μm. The integrated biochip was reacted in a humid chamber at room temperature for one hour, leading to fixation.

Example 3

Confirmation of Phosphorylating Conditions between kinase and substrate using [γ-$^{32}$P]ATP The biochip constructed in Example 2 was washed three times with PBS (200 mM NaCl, 3 mM KCl, 2 mM KH$_2$PO$_4$, 1 mM Na$_2$HPO$_4$, pH 7.5), followed by reaction of the kinase and substrate on the chip. Particularly, the chip was washed with kinase buffer (40 mM Tris-HCl, 20 mM MgCl$_2$, 0.1 mg/ml BSA, pH 7.5) once. Then, 50 μl of kinase reaction solution (kinase buffer containing 100 μM ATP, [γ-$^{32}$P]ATP (0.1~0.6 μCi) (GE Healthcare Life Sciences, UK) and 0.01~50 unit/ml kinase of recombinant Mep45-substrate fusion protein) was distributed on the surface of the biochip. The biochip was covered with cover well, followed by reaction for one hour. One hour later, the biochip was washed with washing buffer three times, followed by washing again with PBS. Centrifugation was performed at 200×g for one minute to eliminate remaining moisture completely. The reacted biochip was sensitized on X-ray film or screen of bioimage analyzer BAS1500 (Fuji Photo Film, Tokyo) for 6-14 hours, followed by measurement of phosphorylation by kinase (FIG. 3).

<3-1> Confirmation of Phosphorylation of cdc2 Protein Kinase-Substrate 1.0 mg/ml of PKTPKKAKKL (SEQ. ID. NO: 2) and Mep45 fusion substrate were integrated on the aldehyde treated slide glass, followed by phosphorylation using 10 unit/ml of cdc2 protein kinase and 0.1 μCi/μl of [γ-$^{32}$P]ATP. Phosphorylation was measured by using X-ray film or X-ray fluorescence spectrometer. BSA (Bovine Serum Albumin) was used for the negative control.

As a result, no signal was detected on the spot of BSA (negative control), while clear signal was detected on the spot of PKTPKKAKKL (SEQ. ID. NO: 2) substrate (FIG. 4A) and Mep45 fusion substrate (FIG. 4B), suggesting that the radio-isotope [γ-$^{32}$P]ATP could be effectively applied for the primary detection of phosphorylation (FIG. 4).

<3-2> Confirmation of Phosphorylation of PKC-Substrate 0.3 mg/ml of AAKIQASFRGHMARKK (SEQ. ID. NO: 1) and Mep45 fusion substrate were integrated on the aldehyde treated slide glass, followed by phosphorylation using 10 unit/ml of PKC and 0.1 μCi/μl of [γ-$^{32}$P]ATP. Phosphorylation was measured by using X-ray film or X-ray fluorescence spectrometer. BSA (Bovine Serum Albumin) was used for the negative control.

As a result, no signal was detected on the spot of BSA (negative control), while clear signal was detected on the spot of AAKIQASFRGHMARKK (SEQ. ID. NO: 1) substrate (FIG. 5A) and Mep45 fusion substrate (FIG. 5B), suggesting that the radio-isotope [γ-$^{32}$P]ATP could be effectively applied for the primary detection of phosphorylation (FIG. 5).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A biochip comprising a fusion protein integrated a matrix surface coated with an active group,
   wherein the fusion protein comprises an elevated protein and a kinase substrate selected from the group consisting of SEQ ID NO: 1-3, wherein the elevated protein is *Selenomonas ruminantium* membrane protein of SEQ ID NO:10.

2. The biochip according to claim 1, wherein the matrix is selected from the group consisting of glass, plastic, metal and silicon.

3. The biochip according to claim 1, wherein the active group is selected from the group consisting of amine group, aldehyde group, carboxyl group and thiol group.

4. The biochip according to claim 1, wherein the kinase is selected from the group consisting of PKC (protein kinase C), cdks (cyclin-dependent protein kinase) and DNA-PK (DNA-dependent protein kinase).

5. The biochip according to claim 1, wherein the fusion protein is integrated as a spot having 100-300 μm diameter and the distance between the spots is 300-500 μm.

6. A kit for the detection of phosphorylation containing the biochip of claim 1 and [γ-$^{32}$P]ATP.

7. The kit for the detection of phosphorylation according to claim 6, wherein the kit additionally contains protein kinase as a positive control.

8. A detection method of phosphorylation comprising the following steps:
   1) mixing a sample with [γ-$^{32}$P]ATP;
   2) inducing phosphorylation by treating the biochip of claim 1 with the mixed sample of step 1);
   3) washing the biochip of step 2); and
   4) measuring phosphorylation by observing signals from the biochip of step 3) using X-ray film and phosphorimager.

9. The detection method of phosphorylation according to claim 8, wherein the sample of step 1) is selected from the group consisting of cell culture solutions, cell lysates, crude extracts of cells or tissues, exudates, and body fluids.

10. The detection method of phosphorylation according to claim 8, wherein step 2) is performed at 30° C. or at 37° C. for 30-60 minutes.

11. The detection method of phosphorylation according to claim 9, wherein the exudates is selected from the group consisting of urine, sweat, saliva and tear.

12. The detection method of phosphorylation according to claim 9, wherein the body fluids is selected from the group consisting of blood, plasma, lymph and serum.

* * * * *

SEQUENCE LISTING

<160> NUMBER OF SEQ ID NOS: 17

<210> SEQ ID NO 1
<211> LENGTH: 16
<212> TYPE: PRT
<213> ORGANISM: Artificial Sequence
<220> FEATURE:
<223> OTHER INFORMATION: Protein Kinase C substrate

<400> SEQUENCE: 1

Ala Ala Lys Ile Gln Ala Ser Phe Arg Gly His Met Ala Arg Lys Lys
1               5                   10                  15

<210> SEQ ID NO 2
<211> LENGTH: 10
<212> TYPE: PRT
<213> ORGANISM: Artificial Sequence
<220> FEATURE:
<223> OTHER INFORMATION: cdc2 Protein Kinase substrate

<400> SEQUENCE: 2

Pro Lys Thr Pro Lys Lys Ala Lys Lys Leu
1               5                   10

<210> SEQ ID NO 3
<211> LENGTH: 15
<212> TYPE: PRT
<213> ORGANISM: Artificial Sequence
<220> FEATURE:
<223> OTHER INFORMATION: DNA-dependent Protein Kinase substrate

<400> SEQUENCE: 3

Glu Pro Pro Leu Ser Gln Gln Ala Phe Ala Asp Leu Trp Lys Lys
1               5                   10                  15

<210> SEQ ID NO 4
<211> LENGTH: 79
<212> TYPE: DNA
<213> ORGANISM: Artificial Sequence
<220> FEATURE:
<223> OTHER INFORMATION: PKC-Fw-Nde primer

<400> SEQUENCE: 4
catcatatgg ctgctaaaat tcaagcttct tttcgtggtc atatggctcg taaaaaagct      60
agcaacccgt tctccgatg                                                   79

<210> SEQ ID NO 5
<211> LENGTH: 85
<212> TYPE: DNA
<213> ORGANISM: Artificial Sequence
<220> FEATURE:
<223> OTHER INFORMATION: PKC-Rv-Bam primer

<400> SEQUENCE: 5
gacggatcct tatttttac gagccatatg accacgaaaa gaagcttgaa ttttagcagc       60
gaagaagaac tgaacgcgac cgaag                                            85

<210> SEQ ID NO 6
<211> LENGTH: 61
<212> TYPE: DNA
<213> ORGANISM: Artificial Sequence
<220> FEATURE:
<223> OTHER INFORMATION: cdc2-MP-Fw-Nde primer -continued

<400> SEQUENCE: 6

```
catcatatgc ctaaaactcc taaaaaagct aaaaaacttg ctagcaaccc gttctccgat    60
g                                                                   61
```

<210> SEQ ID NO 7
<211> LENGTH: 67
<212> TYPE: DNA
<213> ORGANISM: Artificial Sequence
<220> FEATURE:
<223> OTHER INFORMATION: cdc2-MP-Rv-Bam primer

<400> SEQUENCE: 7

```
gacggatcct taaagttttt tagctttttt aggagtttta gggaagaaga actgaacgcg    60
accgaag                                                             67
```

<210> SEQ ID NO 8
<211> LENGTH: 76
<212> TYPE: DNA
<213> ORGANISM: Artificial Sequence
<220> FEATURE:
<223> OTHER INFORMATION: DNA-PK-MP-Fw-Nde primer

<400> SEQUENCE: 8

```
catcatatgg aacctcctct ttctcaacaa gcttttgctg atctttggaa aaaagctagc    60
aacccgttct ccgatg                                                   76
```

<210> SEQ ID NO 9
<211> LENGTH: 82
<212> TYPE: DNA
<213> ORGANISM: Artificial Sequence
<220> FEATURE:
<223> OTHER INFORMATION: DNA-PK-MP-Rv-Bam primer

<400> SEQUENCE: 9

```
gacggatcct tattttttcc aaagatcagc aaaagcttgt tgagaagag gaggttcgaa    60
gaagaactga acgcgaccga ag                                            82
```

<210> SEQ ID NO 10
<211> LENGTH: 432
<212> TYPE: PRT
<213> ORGANISM: Selenomonas ruminantium

<400> SEQUENCE: 10

```
Met Lys Lys Thr Leu Val Ser Ala Leu Thr Thr Ala Leu Val Val Gly
1               5                   10                  15

Ala Ala Ser Thr Thr Phe Ala Ala Ser Asn Pro Phe Ser Asp Val Pro
            20                  25                  30

Ala Asp His Trp Ala Tyr Asp Ala Val Ala Gln Leu Ala Ala Asp Gly
        35                  40                  45

Val Val Glu Gly Tyr Gly Asp Ser Thr Phe Lys Gly Asn Arg Asn Ile
    50                  55                  60

Thr Arg Tyr Glu Met Ala Gln Met Val Ala Lys Ala Met Ala Lys Asn
65                  70                  75                  80

Thr Ser Gly Thr Asp Lys Ala Leu Val Asp Lys Leu Ala Ala Glu Phe
                85                  90                  95

Ala Glu Glu Leu Asn Asn Leu Gly Val Arg Val Ser Asn Leu Glu Arg
            100                 105                 110

Asn Ala Asp Met Val Lys Trp Asn Gly Val Ala Glu Tyr Thr Phe Thr
        115                 120                 125
```

Arg Gln Arg His Glu Lys Asn Gly Lys Lys Thr Thr Asn His Gly Asp
    130                 135                 140

Asp Asn Val Leu Phe Arg Leu Glu Pro Ser Ala Glu Val Asn Ser His
145                 150                 155                 160

Trp His Val Lys Ala Arg Leu Asp Ala Asn Ser Asn Leu Lys Ser Asp
                165                 170                 175

Gln Gly Glu Asp Ser Ser Val Lys Leu Lys Arg Val Trp Ala Gln
            180                 185                 190

Gly Glu Tyr Gly Lys Leu Thr Val Lys Leu Gly Lys Phe Ala Ser Leu
            195                 200                 205

Asn Asp Asp Thr Phe Ala Asp Thr Pro Phe Ser Gly Ala Glu Val Ser
    210                 215                 220

Tyr Gly Lys Asp Val Lys Val Ile Ala Ala Gly Arg Leu Asn Leu
225                 230                 235                 240

Trp Asp Ala Ser Ala Phe Lys Lys Asn Val Asp Ile Gln Asn Val Arg
                245                 250                 255

Asn Trp Met Val Ala Gly Arg His Asp Asp Arg Thr Ala Asn Tyr Gln
                260                 265                 270

Tyr Ala Gly Leu Glu Leu Asn Lys Ser Lys Leu Ser Gly Gly Leu Tyr
            275                 280                 285

Trp His His Leu Asn Ala Ala Gly Phe Asp Tyr Lys Lys Gly Thr Thr
            290                 295                 300

Asp Glu Ala Asn Ile Gly Ala Val Lys Gly Ser Tyr Thr Phe Ser Lys
305                 310                 315                 320

Asn Val Ser Val Asn Gly Phe Tyr Thr Gln Asn Phe Asp Val Asp Thr
                325                 330                 335

Lys Asn Tyr Gln Asp Lys Ser Ala Ser Leu Glu Val Asp Tyr Lys Gly
                340                 345                 350

Ala Gln Gln Glu Asn Lys Gly Thr Trp Gly Ala Trp Val Ala Tyr Arg
            355                 360                 365

Arg Leu Gly Asn Ala Ala Ile Ile Asn Asn Thr Tyr Asp Val Ile Asn
    370                 375                 380

Thr Gly Tyr Lys Gly Trp Glu Val Gly Gly Asn Tyr Thr Leu Phe Lys
385                 390                 395                 400

Asn Val Val Thr Thr Leu Arg Tyr Gly Asn Gln Lys Asp Ile Ser Asn
                405                 410                 415

Ser Asn Val Lys Asp Gln Asn Phe Phe Gly Arg Val Gln Phe Phe
            420                 425                 430

<210> SEQ ID NO 11
<211> LENGTH: 448
<212> TYPE: PRT
<213> ORGANISM: Artificial Sequence
<220> FEATURE:
<223> OTHER INFORMATION: pSrMep45PKC1

<400> SEQUENCE: 11

Ala Ala Lys Ile Gln Ala Ser Phe Arg Gly His Met Ala Arg Lys Lys
1               5                   10                  15

Met Lys Lys Thr Leu Val Ser Ala Leu Thr Thr Ala Leu Val Val Gly
            20                  25                  30

Ala Ala Ser Thr Thr Phe Ala Ala Ser Asn Pro Phe Ser Asp Val Pro
        35                  40                  45

Ala Asp His Trp Ala Tyr Asp Ala Val Ala Gln Leu Ala Ala Asp Gly
    50                  55                  60

```
Val Val Glu Gly Tyr Gly Asp Ser Thr Phe Lys Gly Asn Arg Asn Ile
 65                  70                  75                  80

Thr Arg Tyr Glu Met Ala Gln Met Val Ala Lys Ala Met Ala Lys Asn
                 85                  90                  95

Thr Ser Gly Thr Asp Lys Ala Leu Val Asp Lys Leu Ala Ala Glu Phe
            100                 105                 110

Ala Glu Glu Leu Asn Asn Leu Gly Val Arg Val Ser Asn Leu Glu Arg
        115                 120                 125

Asn Ala Asp Met Val Lys Trp Asn Gly Val Ala Glu Tyr Thr Phe Thr
130                 135                 140

Arg Gln Arg His Glu Lys Asn Gly Lys Lys Thr Thr Asn His Gly Asp
145                 150                 155                 160

Asp Asn Val Leu Phe Arg Leu Glu Pro Ser Ala Glu Val Asn Ser His
                165                 170                 175

Trp His Val Lys Ala Arg Leu Asp Ala Asn Ser Asn Leu Lys Ser Asp
            180                 185                 190

Gln Gly Glu Asp Ser Ser Val Lys Leu Lys Arg Val Trp Ala Gln
        195                 200                 205

Gly Glu Tyr Gly Lys Leu Thr Val Lys Leu Gly Lys Phe Ala Ser Leu
210                 215                 220

Asn Asp Asp Thr Phe Ala Asp Thr Pro Phe Ser Gly Ala Glu Val Ser
225                 230                 235                 240

Tyr Gly Lys Asp Val Lys Val Ile Ala Ala Gly Arg Leu Asn Leu
                245                 250                 255

Trp Asp Ala Ser Ala Phe Lys Lys Asn Val Asp Ile Gln Asn Val Arg
            260                 265                 270

Asn Trp Met Val Ala Gly Arg His Asp Arg Thr Ala Asn Tyr Gln
                275                 280                 285

Tyr Ala Gly Leu Glu Leu Asn Lys Ser Lys Leu Ser Gly Gly Leu Tyr
290                 295                 300

Trp His His Leu Asn Ala Ala Gly Phe Asp Tyr Lys Lys Gly Thr Thr
305                 310                 315                 320

Asp Glu Ala Asn Ile Gly Ala Val Lys Gly Ser Tyr Thr Phe Ser Lys
                325                 330                 335

Asn Val Ser Val Asn Gly Phe Tyr Thr Gln Asn Phe Asp Val Asp Thr
            340                 345                 350

Lys Asn Tyr Gln Asp Lys Ser Ala Ser Leu Glu Val Asp Tyr Lys Gly
                355                 360                 365

Ala Gln Gln Glu Asn Lys Gly Thr Trp Gly Ala Trp Val Ala Tyr Arg
370                 375                 380

Arg Leu Gly Asn Ala Ala Ile Ile Asn Asn Thr Tyr Asp Val Ile Asn
385                 390                 395                 400

Thr Gly Tyr Lys Gly Trp Glu Val Gly Gly Asn Tyr Thr Leu Phe Lys
                405                 410                 415

Asn Val Val Thr Thr Leu Arg Tyr Gly Asn Gln Lys Asp Ile Ser Asn
            420                 425                 430

Ser Asn Val Lys Asp Gln Asn Phe Phe Gly Arg Val Gln Phe Phe Phe
        435                 440                 445

<210> SEQ ID NO 12
<211> LENGTH: 464
<212> TYPE: PRT
<213> ORGANISM: Artificial Sequence
<220> FEATURE:
```

<223> OTHER INFORMATION: pSrMep45PKC2

<400> SEQUENCE: 12

```
Ala Ala Lys Ile Gln Ala Ser Phe Arg Gly His Met Ala Arg Lys Lys
1               5                   10                  15

Met Lys Lys Thr Leu Val Ser Ala Leu Thr Thr Ala Leu Val Val Gly
            20                  25                  30

Ala Ala Ser Thr Thr Phe Ala Ala Ser Asn Pro Phe Ser Asp Val Pro
        35                  40                  45

Ala Asp His Trp Ala Tyr Asp Ala Val Ala Gln Leu Ala Ala Asp Gly
    50                  55                  60

Val Val Glu Gly Tyr Gly Asp Ser Thr Phe Lys Gly Asn Arg Asn Ile
65                  70                  75                  80

Thr Arg Tyr Glu Met Ala Gln Met Val Lys Ala Met Ala Lys Asn
                85                  90                  95

Thr Ser Gly Thr Asp Lys Ala Leu Val Asp Lys Leu Ala Ala Glu Phe
            100                 105                 110

Ala Glu Glu Leu Asn Asn Leu Gly Val Arg Val Ser Asn Leu Glu Arg
        115                 120                 125

Asn Ala Asp Met Val Lys Trp Asn Gly Val Ala Glu Tyr Thr Phe Thr
130                 135                 140

Arg Gln Arg His Glu Lys Asn Gly Lys Lys Thr Thr Asn His Gly Asp
145                 150                 155                 160

Asp Asn Val Leu Phe Arg Leu Glu Pro Ser Ala Glu Val Asn Ser His
                165                 170                 175

Trp His Val Lys Ala Arg Leu Asp Ala Asn Ser Asn Leu Lys Ser Asp
            180                 185                 190

Gln Gly Glu Asp Ser Ser Val Lys Leu Lys Arg Val Trp Ala Gln
        195                 200                 205

Gly Glu Tyr Gly Lys Leu Thr Val Lys Leu Gly Lys Phe Ala Ser Leu
210                 215                 220

Asn Asp Asp Thr Phe Ala Asp Thr Pro Phe Ser Gly Ala Glu Val Ser
225                 230                 235                 240

Tyr Gly Lys Asp Val Lys Val Ile Ala Ala Ala Gly Arg Leu Asn Leu
                245                 250                 255

Trp Asp Ala Ser Ala Phe Lys Lys Asn Val Asp Ile Gln Asn Val Arg
            260                 265                 270

Asn Trp Met Val Ala Gly Arg His Asp Asp Arg Thr Ala Asn Tyr Gln
        275                 280                 285

Tyr Ala Gly Leu Glu Leu Asn Lys Ser Lys Leu Ser Gly Gly Leu Tyr
290                 295                 300

Trp His His Leu Asn Ala Ala Gly Phe Asp Tyr Lys Lys Gly Thr Thr
305                 310                 315                 320

Asp Glu Ala Asn Ile Gly Ala Val Lys Gly Ser Tyr Thr Phe Ser Lys
                325                 330                 335

Asn Val Ser Val Asn Gly Phe Tyr Thr Gln Asn Phe Asp Val Asp Thr
            340                 345                 350

Lys Asn Tyr Gln Asp Lys Ser Ala Ser Leu Glu Val Asp Tyr Lys Gly
        355                 360                 365

Ala Gln Gln Glu Asn Lys Gly Thr Trp Gly Ala Trp Val Ala Tyr Arg
370                 375                 380

Arg Leu Gly Asn Ala Ala Ile Ile Asn Asn Thr Tyr Asp Val Ile Asn
385                 390                 395                 400
```

```
Thr Gly Tyr Lys Gly Trp Glu Val Gly Gly Asn Tyr Thr Leu Phe Lys
            405                 410                 415

Asn Val Val Thr Thr Leu Arg Tyr Gly Asn Gln Lys Asp Ile Ser Asn
        420                 425                 430

Ser Asn Val Lys Asp Gln Asn Phe Phe Gly Arg Val Gln Phe Phe Phe
        435                 440                 445

Ala Ala Lys Ile Gln Ala Ser Phe Arg Gly His Met Ala Arg Lys Lys
    450                 455                 460

<210> SEQ ID NO 13
<211> LENGTH: 442
<212> TYPE: PRT
<213> ORGANISM: Artificial Sequence
<220> FEATURE:
<223> OTHER INFORMATION: pSrMep45cdc21

<400> SEQUENCE: 13

Pro Lys Thr Pro Lys Lys Ala Lys Lys Leu Met Lys Lys Thr Leu Val
1               5                   10                  15

Ser Ala Leu Thr Thr Ala Leu Val Val Gly Ala Ala Ser Thr Thr Phe
            20                  25                  30

Ala Ala Ser Asn Pro Phe Ser Asp Val Pro Ala Asp His Trp Ala Tyr
        35                  40                  45

Asp Ala Val Ala Gln Leu Ala Ala Asp Gly Val Val Glu Gly Tyr Gly
    50                  55                  60

Asp Ser Thr Phe Lys Gly Asn Arg Asn Ile Thr Arg Tyr Glu Met Ala
65                  70                  75                  80

Gln Met Val Ala Lys Ala Met Ala Lys Asn Thr Ser Gly Thr Asp Lys
                85                  90                  95

Ala Leu Val Asp Lys Leu Ala Ala Glu Phe Ala Glu Glu Leu Asn Asn
            100                 105                 110

Leu Gly Val Arg Val Ser Asn Leu Glu Arg Asn Ala Asp Met Val Lys
        115                 120                 125

Trp Asn Gly Val Ala Glu Tyr Thr Phe Thr Arg Gln Arg His Glu Lys
    130                 135                 140

Asn Gly Lys Lys Thr Thr Asn His Gly Asp Asp Asn Val Leu Phe Arg
145                 150                 155                 160

Leu Glu Pro Ser Ala Glu Val Asn Ser His Trp His Val Lys Ala Arg
                165                 170                 175

Leu Asp Ala Asn Ser Asn Leu Lys Ser Asp Gln Gly Glu Asp Ser Ser
            180                 185                 190

Ser Val Lys Leu Lys Arg Val Trp Ala Gln Gly Glu Tyr Gly Lys Leu
        195                 200                 205

Thr Val Lys Leu Gly Lys Phe Ala Ser Leu Asn Asp Asp Thr Phe Ala
    210                 215                 220

Asp Thr Pro Phe Ser Gly Ala Glu Val Ser Tyr Gly Lys Asp Val Lys
225                 230                 235                 240

Val Ile Ala Ala Ala Gly Arg Leu Asn Leu Trp Asp Ala Ser Ala Phe
                245                 250                 255

Lys Lys Asn Val Asp Ile Gln Asn Val Arg Asn Trp Met Val Ala Gly
            260                 265                 270

Arg His Asp Asp Arg Thr Ala Asn Tyr Gln Tyr Ala Gly Leu Glu Leu
        275                 280                 285

Asn Lys Ser Lys Leu Ser Gly Gly Leu Tyr Trp His His Leu Asn Ala
    290                 295                 300
```

```
Ala Gly Phe Asp Tyr Lys Lys Gly Thr Thr Asp Glu Ala Asn Ile Gly
305                 310                 315                 320

Ala Val Lys Gly Ser Tyr Thr Phe Ser Lys Asn Val Ser Val Asn Gly
                325                 330                 335

Phe Tyr Thr Gln Asn Phe Asp Val Asp Thr Lys Asn Tyr Gln Asp Lys
            340                 345                 350

Ser Ala Ser Leu Glu Val Asp Tyr Lys Gly Ala Gln Gln Glu Asn Lys
        355                 360                 365

Gly Thr Trp Gly Ala Trp Val Ala Tyr Arg Arg Leu Gly Asn Ala Ala
    370                 375                 380

Ile Ile Asn Asn Thr Tyr Asp Val Ile Asn Thr Gly Tyr Lys Gly Trp
385                 390                 395                 400

Glu Val Gly Gly Asn Tyr Thr Leu Phe Lys Asn Val Val Thr Thr Leu
                405                 410                 415

Arg Tyr Gly Asn Gln Lys Asp Ile Ser Asn Ser Asn Val Lys Asp Gln
            420                 425                 430

Asn Phe Phe Gly Arg Val Gln Phe Phe
        435                 440

<210> SEQ ID NO 14
<211> LENGTH: 452
<212> TYPE: PRT
<213> ORGANISM: Artificial Sequence
<220> FEATURE:
<223> OTHER INFORMATION: pSrMep45cdc22

<400> SEQUENCE: 14

Pro Lys Thr Pro Lys Lys Ala Lys Lys Leu Met Lys Lys Thr Leu Val
1               5                   10                  15

Ser Ala Leu Thr Thr Ala Leu Val Val Gly Ala Ala Ser Thr Thr Phe
            20                  25                  30

Ala Ala Ser Asn Pro Phe Ser Asp Val Pro Ala Asp His Trp Ala Tyr
        35                  40                  45

Asp Ala Val Ala Gln Leu Ala Ala Asp Gly Val Val Glu Gly Tyr Gly
    50                  55                  60

Asp Ser Thr Phe Lys Gly Asn Arg Asn Ile Thr Arg Tyr Glu Met Ala
65                  70                  75                  80

Gln Met Val Ala Lys Ala Met Lys Asn Thr Ser Gly Thr Asp Lys
                85                  90                  95

Ala Leu Val Asp Lys Leu Ala Ala Glu Phe Ala Glu Glu Leu Asn Asn
            100                 105                 110

Leu Gly Val Arg Val Ser Asn Leu Glu Arg Asn Ala Asp Met Val Lys
        115                 120                 125

Trp Asn Gly Val Ala Glu Tyr Thr Phe Thr Arg Gln Arg His Glu Lys
    130                 135                 140

Asn Gly Lys Lys Thr Thr Asn His Gly Asp Asn Val Leu Phe Arg
145                 150                 155                 160

Leu Glu Pro Ser Ala Glu Val Asn Ser His Trp His Val Lys Ala Arg
                165                 170                 175

Leu Asp Ala Asn Ser Asn Leu Lys Ser Asp Gln Gly Glu Asp Ser Ser
            180                 185                 190

Ser Val Lys Leu Lys Arg Val Trp Ala Gln Gly Glu Tyr Gly Lys Leu
        195                 200                 205

Thr Val Lys Leu Gly Lys Phe Ala Ser Leu Asn Asp Asp Thr Phe Ala
    210                 215                 220
```

```
Asp Thr Pro Phe Ser Gly Ala Glu Val Ser Tyr Gly Lys Asp Val Lys
225                 230                 235                 240

Val Ile Ala Ala Ala Gly Arg Leu Asn Leu Trp Asp Ala Ser Ala Phe
                245                 250                 255

Lys Lys Asn Val Asp Ile Gln Asn Val Arg Asn Trp Met Val Ala Gly
            260                 265                 270

Arg His Asp Asp Arg Thr Ala Asn Tyr Gln Tyr Ala Gly Leu Glu Leu
        275                 280                 285

Asn Lys Ser Lys Leu Ser Gly Gly Leu Tyr Trp His His Leu Asn Ala
    290                 295                 300

Ala Gly Phe Asp Tyr Lys Lys Gly Thr Thr Asp Glu Ala Asn Ile Gly
305                 310                 315                 320

Ala Val Lys Gly Ser Tyr Thr Phe Ser Lys Asn Val Ser Val Asn Gly
                325                 330                 335

Phe Tyr Thr Gln Asn Phe Asp Val Asp Thr Lys Asn Tyr Gln Asp Lys
            340                 345                 350

Ser Ala Ser Leu Glu Val Asp Tyr Lys Gly Ala Gln Gln Glu Asn Lys
        355                 360                 365

Gly Thr Trp Gly Ala Trp Val Ala Tyr Arg Arg Leu Gly Asn Ala Ala
    370                 375                 380

Ile Ile Asn Asn Thr Tyr Asp Val Ile Asn Thr Gly Tyr Lys Gly Trp
385                 390                 395                 400

Glu Val Gly Gly Asn Tyr Thr Leu Phe Lys Asn Val Val Thr Thr Leu
                405                 410                 415

Arg Tyr Gly Asn Gln Lys Asp Ile Ser Asn Ser Asn Val Lys Asp Gln
            420                 425                 430

Asn Phe Phe Gly Arg Val Gln Phe Phe Pro Lys Thr Pro Lys Lys
        435                 440                 445

Ala Lys Lys Leu
    450

<210> SEQ ID NO 15
<211> LENGTH: 447
<212> TYPE: PRT
<213> ORGANISM: Artificial Sequence
<220> FEATURE:
<223> OTHER INFORMATION: pSrMep45DPK1

<400> SEQUENCE: 15

Glu Pro Pro Leu Ser Gln Gln Ala Phe Ala Asp Leu Trp Lys Lys Met
1               5                   10                  15

Lys Lys Thr Leu Val Ser Ala Leu Thr Thr Ala Leu Val Val Gly Ala
            20                  25                  30

Ala Ser Thr Thr Phe Ala Ala Ser Asn Pro Phe Ser Asp Val Pro Ala
        35                  40                  45

Asp His Trp Ala Tyr Asp Ala Val Ala Gln Leu Ala Ala Asp Gly Val
    50                  55                  60

Val Glu Gly Tyr Gly Asp Ser Thr Phe Lys Gly Asn Arg Asn Ile Thr
65              70                  75                  80

Arg Tyr Glu Met Ala Gln Met Val Ala Lys Ala Met Ala Lys Asn Thr
                85                  90                  95

Ser Gly Thr Asp Lys Ala Leu Val Asp Lys Leu Ala Ala Glu Phe Ala
            100                 105                 110

Glu Glu Leu Asn Asn Leu Gly Val Arg Val Ser Asn Leu Glu Arg Asn
        115                 120                 125
```

```
Ala Asp Met Val Lys Trp Asn Gly Val Ala Glu Tyr Thr Phe Thr Arg
    130                 135                 140

Gln Arg His Glu Lys Asn Gly Lys Lys Thr Thr Asn His Gly Asp Asp
145                 150                 155                 160

Asn Val Leu Phe Arg Leu Glu Pro Ser Ala Glu Val Asn Ser His Trp
                165                 170                 175

His Val Lys Ala Arg Leu Asp Ala Asn Ser Asn Leu Lys Ser Asp Gln
            180                 185                 190

Gly Glu Asp Ser Ser Ser Val Lys Leu Lys Arg Val Trp Ala Gln Gly
        195                 200                 205

Glu Tyr Gly Lys Leu Thr Val Lys Leu Gly Lys Phe Ala Ser Leu Asn
210                 215                 220

Asp Asp Thr Phe Ala Asp Thr Pro Phe Ser Gly Ala Glu Val Ser Tyr
225                 230                 235                 240

Gly Lys Asp Val Lys Val Ile Ala Ala Ala Gly Arg Leu Asn Leu Trp
                245                 250                 255

Asp Ala Ser Ala Phe Lys Lys Asn Val Asp Ile Gln Asn Val Arg Asn
            260                 265                 270

Trp Met Val Ala Gly Arg His Asp Asp Arg Thr Ala Asn Tyr Gln Tyr
        275                 280                 285

Ala Gly Leu Glu Leu Asn Lys Ser Lys Leu Ser Gly Gly Leu Tyr Trp
290                 295                 300

His His Leu Asn Ala Ala Gly Phe Asp Tyr Lys Lys Gly Thr Thr Asp
305                 310                 315                 320

Glu Ala Asn Ile Gly Ala Val Lys Gly Ser Tyr Thr Phe Ser Lys Asn
                325                 330                 335

Val Ser Val Asn Gly Phe Tyr Thr Gln Asn Phe Asp Val Asp Thr Lys
            340                 345                 350

Asn Tyr Gln Asp Lys Ser Ala Ser Leu Glu Val Asp Tyr Lys Gly Ala
        355                 360                 365

Gln Gln Glu Asn Lys Gly Thr Trp Gly Ala Trp Val Ala Tyr Arg Arg
    370                 375                 380

Leu Gly Asn Ala Ala Ile Ile Asn Asn Thr Tyr Asp Val Ile Asn Thr
385                 390                 395                 400

Gly Tyr Lys Gly Trp Glu Val Gly Gly Asn Tyr Thr Leu Phe Lys Asn
                405                 410                 415

Val Val Thr Thr Leu Arg Tyr Gly Asn Gln Lys Asp Ile Ser Asn Ser
            420                 425                 430

Asn Val Lys Asp Gln Asn Phe Phe Gly Arg Val Gln Phe Phe Phe
        435                 440                 445

<210> SEQ ID NO 16
<211> LENGTH: 462
<212> TYPE: PRT
<213> ORGANISM: Artificial Sequence
<220> FEATURE:
<223> OTHER INFORMATION: pSrMep45DPK2

<400> SEQUENCE: 16

Glu Pro Pro Leu Ser Gln Gln Ala Phe Ala Asp Leu Trp Lys Lys Met
1               5                   10                  15

Lys Lys Thr Leu Val Ser Ala Leu Thr Thr Ala Leu Val Val Gly Ala
            20                  25                  30

Ala Ser Thr Thr Phe Ala Ala Ser Asn Pro Phe Ser Asp Val Pro Ala
        35                  40                  45
```

-continued

```
Asp His Trp Ala Tyr Asp Ala Val Ala Gln Leu Ala Ala Asp Gly Val
 50                  55                  60
Val Glu Gly Tyr Gly Asp Ser Thr Phe Lys Gly Asn Arg Asn Ile Thr
 65                  70                  75                  80
Arg Tyr Glu Met Ala Gln Met Val Ala Lys Ala Met Ala Lys Asn Thr
                 85                  90                  95
Ser Gly Thr Asp Lys Ala Leu Val Asp Lys Leu Ala Ala Glu Phe Ala
                100                 105                 110
Glu Glu Leu Asn Asn Leu Gly Val Arg Val Ser Asn Leu Glu Arg Asn
                115                 120                 125
Ala Asp Met Val Lys Trp Asn Gly Val Ala Glu Tyr Thr Phe Thr Arg
    130                 135                 140
Gln Arg His Glu Lys Asn Gly Lys Lys Thr Thr Asn His Gly Asp Asp
145                 150                 155                 160
Asn Val Leu Phe Arg Leu Glu Pro Ser Ala Glu Val Asn Ser His Trp
                165                 170                 175
His Val Lys Ala Arg Leu Asp Ala Asn Ser Asn Leu Lys Ser Asp Gln
                180                 185                 190
Gly Glu Asp Ser Ser Val Lys Leu Lys Arg Val Trp Ala Gln Gly
                195                 200                 205
Glu Tyr Gly Lys Leu Thr Val Lys Leu Gly Lys Phe Ala Ser Leu Asn
    210                 215                 220
Asp Asp Thr Phe Ala Asp Thr Pro Phe Ser Gly Ala Glu Val Ser Tyr
225                 230                 235                 240
Gly Lys Asp Val Lys Val Ile Ala Ala Gly Arg Leu Asn Leu Trp
                245                 250                 255
Asp Ala Ser Ala Phe Lys Lys Asn Val Asp Ile Gln Asn Val Arg Asn
                260                 265                 270
Trp Met Val Ala Gly Arg His Asp Asp Arg Thr Ala Asn Tyr Gln Tyr
    275                 280                 285
Ala Gly Leu Glu Leu Asn Lys Ser Lys Leu Ser Gly Gly Leu Tyr Trp
    290                 295                 300
His His Leu Asn Ala Ala Gly Phe Asp Tyr Lys Lys Gly Thr Thr Asp
305                 310                 315                 320
Glu Ala Asn Ile Gly Ala Val Lys Gly Ser Tyr Thr Phe Ser Lys Asn
                325                 330                 335
Val Ser Val Asn Gly Phe Tyr Thr Gln Asn Phe Asp Val Asp Thr Lys
                340                 345                 350
Asn Tyr Gln Asp Lys Ser Ala Ser Leu Glu Val Asp Tyr Lys Gly Ala
    355                 360                 365
Gln Gln Glu Asn Lys Gly Thr Trp Gly Ala Trp Val Ala Tyr Arg Arg
    370                 375                 380
Leu Gly Asn Ala Ala Ile Ile Asn Asn Thr Tyr Asp Val Ile Asn Thr
385                 390                 395                 400
Gly Tyr Lys Gly Trp Glu Val Gly Gly Asn Tyr Thr Leu Phe Lys Asn
                405                 410                 415
Val Val Thr Thr Leu Arg Tyr Gly Asn Gln Lys Asp Ile Ser Asn Ser
                420                 425                 430
Asn Val Lys Asp Gln Asn Phe Phe Gly Arg Val Gln Phe Phe Phe Glu
    435                 440                 445
Pro Pro Leu Ser Gln Gln Ala Phe Ala Asp Leu Trp Lys Lys
450                 455                 460
```

<210> SEQ ID NO 17
<211> LENGTH: 2239
<212> TYPE: DNA
<213> ORGANISM: Selenomonas ruminantium

<400> SEQUENCE: 17

| | | | | | |
|---|---|---|---|---|---|
| agagcctatg | agccctatga | ggtcctgatg | gatatcagcc | gcaagctcac | ggatgtgggg | 60 |
| gtgttgtacg | gcgatttcct | caatgtgcgc | tataccggcg | tattggaggc | gttgcaaaac | 120 |
| ggggaatttc | ctgtgcggga | aaaacatctt | tatgccaaga | gcgaaatggt | gcggctgctg | 180 |
| gatgataccc | tgtttaagga | aatcgatttt | gtgcccggcg | ccctggacga | tgatgaacaa | 240 |
| attgcccgca | gctgggaaga | gcaggggtat | gtgaatatcc | agcatgaagt | ggctgtcagc | 300 |
| ccatatctgt | tccgggctgc | tgtcagcact | gccagcgttg | ctaatctcaa | gagcctatac | 360 |
| actccggaag | tacgtaagga | actggcgcgg | attctccatc | ggatcgagta | tgacgtgcag | 420 |
| cgggcggata | atataatgcg | gctgcaacaa | ctgtgcaaac | aggaaggcat | tttctcagag | 480 |
| tatttgcagg | attttataga | agaaacatgt | tatcatgcaa | atgaagtaaa | acatttgttg | 540 |
| ccagatgaac | aatgagactc | aaagtcaaat | aaaagttgtc | agacacttgc | aaattgctat | 600 |
| tatctatgat | aaaattagcg | ttgtcttgga | aatggattag | gatttgctga | ggaaacatgg | 660 |
| acactcatgg | aaagaataat | ccgccttcaa | gacgagtact | aacactattt | attgaaggag | 720 |
| gagtttctta | tgaagaagac | tctcgtatcc | gctctgacga | ccgctctggt | tgttggtgca | 780 |
| gctagcacga | cgtttgctgc | tagcaacccg | ttctccgatg | ttcctgctga | tcattgggct | 840 |
| tatgacgctg | tagctcagct | ggctgctgac | ggcgttgttg | aaggttatgg | cgacagcacc | 900 |
| ttcaagggca | accgtaacat | cactcgttac | gaaatggctc | agatggttgc | taaagctatg | 960 |
| gctaagaaca | cttccggcac | ggacaaggct | ctggttgaca | aactggctgc | tgaattcgca | 1020 |
| gaagaactca | caaacctcgg | tgttcgcgta | agcaacctcg | aacgcaatgc | tgacatggtt | 1080 |
| aaatggaatg | gcgttgctga | gtacaccttc | acgcgtcagc | gtcatgaaaa | aaatggcaaa | 1140 |
| aagacgacga | atcatggcga | cgacaatgta | ctgttccgtc | tcgagccctc | cgctgaagtt | 1200 |
| aacagccatt | ggcatgtaaa | ggctcgtctc | gatgctaact | ccaacctgaa | atctgaccag | 1260 |
| ggtgaagata | gcagcagcgt | taagctgaaa | cgtgtatggg | ctcagggtga | atatggcaaa | 1320 |
| ctgacggtta | aactcggtaa | gtttgcttcc | ctgaacgacg | atacctttgc | tgatacgccg | 1380 |
| ttctccggtg | ctgaagtttc | ctacggcaag | gatgttaaag | tcattgctgc | tgctggtcgt | 1440 |
| ctgaaccttt | gggatgctag | tgcatttaag | aagaatgtag | acatccagaa | tgttcgtaat | 1500 |
| tggatggttg | ctggtcgtca | cgatgataga | actgcaaact | atcagtatgc | tggtctcgaa | 1560 |
| ctcaacaaga | gcaagctgag | cggtggcctg | tactggcatc | acctgaacgc | agcaggtttc | 1620 |
| gattataaga | aggtacgac | ggatgaagct | aatatcggtg | cagtaaaagg | cagctacacc | 1680 |
| tttagcaaga | atgtcagcgt | aaatggtttc | tatactcaga | actttgatgt | tgataccaag | 1740 |
| aattatcagg | ataagtccgc | tagcctcgaa | gtagactata | agggcgctca | gcaggaaaac | 1800 |
| aagggtactt | ggggtgcttg | ggttgcatac | cgtcgccttg | gtaacgccgc | aatcatcaac | 1860 |
| aacacgtacg | atgttatcaa | tacgggctac | aaaggttggg | aagttggcgg | taactacacg | 1920 |
| ctcttcaaga | acgttgtaac | gactctccgt | tatggcaacc | agaaggatat | cagcaactcc | 1980 |
| aacgttaagg | accagaattt | cttcggtcgc | gttcagttct | tcttctaatc | ctgagattag | 2040 |
| cagattatac | gcaaataaca | aagacctccg | ttgtggcgga | ggtctttcct | tgcaataagc | 2100 |
| agggatttgt | agtagaatga | acatagataa | aaaaagacca | ccgatagacg | gctagtttcc | 2160 |

-continued

```
acgctcgatg gttaatagct taataagaaa cagaaataac cgtcaagctt ggacccttgg    2220
gcggttattt ttgtttcag                                                 2239
```